(12) United States Patent
Isitani et al.

(10) Patent No.: US 7,258,771 B2
(45) Date of Patent: Aug. 21, 2007

(54) AIR/FUEL RATIO DETECTION APPARATUS

(75) Inventors: Shigeo Isitani, Gunma (JP); Yasuji Orimo, Gunma (JP); Chiharu Katsuyama, Gunma (JP); Futoshi Ichiyanagi, Gunma (JP)

(73) Assignee: Hitachi, Ltd., Tokyo (JP)

( * ) Notice: Subject to any disclaimer, the term of this patent is extended or adjusted under 35 U.S.C. 154(b) by 304 days.

(21) Appl. No.: 10/217,534

(22) Filed: Aug. 14, 2002

(65) Prior Publication Data

US 2003/0052004 A1  Mar. 20, 2003

(30) Foreign Application Priority Data

Sep. 17, 2001 (JP) .............................. 2001-282185

(51) Int. Cl.
*G01N 27/41* (2006.01)
(52) U.S. Cl. .................. 204/425; 156/89.12; 73/23.32
(58) Field of Classification Search ........ 204/424–429; 73/23.31, 23.32; 205/785, 787; 156/89.12
See application file for complete search history.

(56) References Cited

U.S. PATENT DOCUMENTS

| | | | | |
|---|---|---|---|---|
| 4,642,174 | A | * | 2/1987 | Shibata ........................ 204/408 |
| 4,718,999 | A | * | 1/1988 | Suzuki et al. ................ 204/406 |
| 4,980,042 | A | * | 12/1990 | Shiomi et al. ............... 204/427 |
| 5,139,829 | A | * | 8/1992 | Minoha et al. .............. 427/123 |
| 5,507,174 | A | | 4/1996 | Friese et al. |
| 5,763,763 | A | * | 6/1998 | Kato et al. ................... 205/781 |
| 5,948,225 | A | * | 9/1999 | Katafuchi et al. ........... 204/421 |
| 6,533,911 | B1 | * | 3/2003 | Fujita et al. ................. 204/424 |

FOREIGN PATENT DOCUMENTS

| | | |
|---|---|---|
| DE | 197-44-224 C2 | 4/1999 |
| DE | 199 49 300 A1 | 5/2001 |
| JP | 61-10762 | 1/1986 |
| JP | 61-100651 | 5/1986 |
| JP | 7-501152 | 2/1995 |

OTHER PUBLICATIONS

Translation of JP 61-100651, May 1986.*

* cited by examiner

*Primary Examiner*—Kaj K. Olsen
(74) *Attorney, Agent, or Firm*—Sughrue Mion, PLLC

(57) ABSTRACT

The invention relates to an air/fuel ratio detection apparatus. This apparatus includes (a) a heater portion having an elongate cylindrical shape and heating by applying electricity thereto from outside; (b) a solid electrolyte layer surrounding the heater portion and being activated by heat to conduct oxygen ions therethrough; (c) first and second electrodes in contact with the solid electrolyte layer and being away from each other such that pumping voltage is applied by the first and second electrodes to the solid electrolyte layer; (d) a reference electrode for outputting an air/fuel ratio detection signal, the reference electrode being formed on the solid electrolyte layer and being away from the first and second electrodes; and (e) a diffusion layer made of a porous material and surrounding periphery of the solid electrolyte layer to cover the first and second electrodes and the reference electrode.

10 Claims, 12 Drawing Sheets

AIR/FUEL RATIO DETECTION APPARATUS

BACKGROUND OF THE INVENTION

The present invention relates to an air/fuel ratio detection apparatus for determining air/fuel ratio of, for example, automotive engines from oxygen concentration or the like of exhaust gas.

In general, automotive engines and the like are provided with an air/fuel ratio sensor (oxygen sensor) in the middle of exhaust pipe or the like for detecting oxygen concentration or the like of exhaust gas.

The air/fuel ratio sensor outputs air/fuel ratio detection signal. Based on this signal, it is possible to conduct a feed-back control of the amount of fuel injection, thereby achieving stoichiometric air/fuel ratio (A/F=14.7) or lean air/fuel ratio (A/F≧15). With this, it is possible to improve engine combustion efficiency and fuel consumption.

There are such conventional air/fuel ratio sensors, which are plate-like in shape (see Japanese Patent Laid-open (Kokai) Publication Showa 61(1986)-10762, Japanese Patent Laid-open (Kokai) Publication Showa 61(1986)-100651, and Japanese Patent Laid-open (Kohyo) Publication Heisei 7(1995)-501152 corresponding to U.S. Pat. No. 5,507,174). These plate-like air-fuel ratio sensors include a heater portion and a solid electrolyte layer and a diffusion layer, which are formed on one major surface of the heater portion.

There are recent demands for the improvement in productivity of air/fuel ratio sensors and for freedom in the direction of installation of air/fuel ratio sensors. With this freedom, it becomes possible to improve the accuracy for detecting oxygen concentration and the like and thereby to properly control the amount of fuel injection and stabilize the engine control. Furthermore, there are recent demands for the rapid temperature increase of the heater portion of air/fuel ratio sensors after the engine starts. With this rapid increase, it becomes possible to shorten the period of time required for activating the solid electrolyte layer and the like, thereby shorten the period of time required for enabling the measurement of oxygen concentration and the like. This makes it possible to properly conduct a feedback control of the amount of fuel injection, based on the signal from air/fuel ratio sensors, at an early stage after the engine starts.

SUMMARY OF THE INVENTION

It is an object of the present invention to provide an air/fuel ratio detection apparatus, which makes it possible to improve accuracy and stability in detecting oxygen concentration of exhaust gas and to shorten the period of time for increasing the temperature of its heater portion and for enabling the air/fuel ratio detection at an early stage after the engine starts.

According to the present invention, there is provided an air/fuel ratio detection apparatus comprising:

a heater portion that has an elongate cylindrical shape and heats by applying electricity to the heater portion from an outside;

a solid electrolyte layer formed on and surrounding periphery of the heater portion, the solid electrolyte layer being activated by heat from the heater portion to conduct oxygen ions through the solid electrolyte layer;

first and second electrodes that are in contact with the solid electrolyte layer and are away from each other such that a pumping voltage supplied from an outside is applied by the first and second electrodes to the solid electrolyte layer;

a reference electrode for outputting an air/fuel ratio detection signal in relation to one of the first and second electrodes, the reference electrode being formed on the solid electrolyte layer and being away from the first and second electrodes; and a diffusion layer made of a porous material, the diffusion layer being formed on and surrounding periphery of the solid electrolyte layer to cover the first and second electrodes and the reference electrode.

The other objects and features of this invention will become understood from the following description with reference to the accompanying drawings.

DESCRIPTION OF THE PREFERRED EMBODIMENTS

As stated above, an air/fuel ratio detection apparatus according to the present invention has a heater portion that has an elongate cylindrical shape. Thus, it is possible to form a solid electrolyte layer, a diffusion layer and the like on the periphery of the heater portion using technique such as curved surface printing. Therefore, it is possible to form the air/fuel ratio detection apparatus as a whole into an elongate cylindrical shape, as show in FIG. 1. This elongate cylindrical shape can provide more freedom in selecting the direction of installation of the air/fuel ratio detection apparatus. This makes it possible to detect oxygen concentration and the like of exhaust gas with a stable accuracy. Furthermore, it becomes possible to have an enlarged heating surface area of the heater portion for heating the solid electrolyte layer. With this, it becomes possible to efficiently transmit heat from the heater portion towards the solid electrolyte layer and the like. Therefore, it becomes possible to shorten the period of time for increasing the temperature of the heater portion, thereby activating the solid electrolyte layer early. This makes it possible to stably and accurately detect or determine air/fuel ratio at an early stage after the engine starts, thereby instantly conducting feedback control. Furthermore, it is not necessary to introduce the air (as a standard) into the inside of the air/fuel ratio detection device. Therefore, the air/fuel ratio detection apparatus is simplified in structure, thereby improving workability for producing the same. Furthermore, the heater portion is reduced in electric power consumption.

Furthermore, the air/fuel ratio detection apparatus is clearly made by its elongate cylindrical shape to have a smaller size, as compared with conventional plate-like air/fuel ratio detection apparatuses, while providing each of the first and second electrodes and the reference electrode with a sufficient area.

By applying pumping voltage between the first and second electrodes, it is possible to detect a diffusion limiting current (pumping current) corresponding to the oxygen concentration of an exhaust gas when the exhaust gas is in a lean condition and to detect a diffusion limiting current corresponding to combustible gas components concentration of an exhaust gas when the exhaust gas is in a rich condition.

With reference to FIGS. 1-14, a first air/fuel ratio detection apparatus (first air/fuel ratio or oxygen sensor) according to a first embodiment of the present invention will be described in detail in the following.

Figure 1:
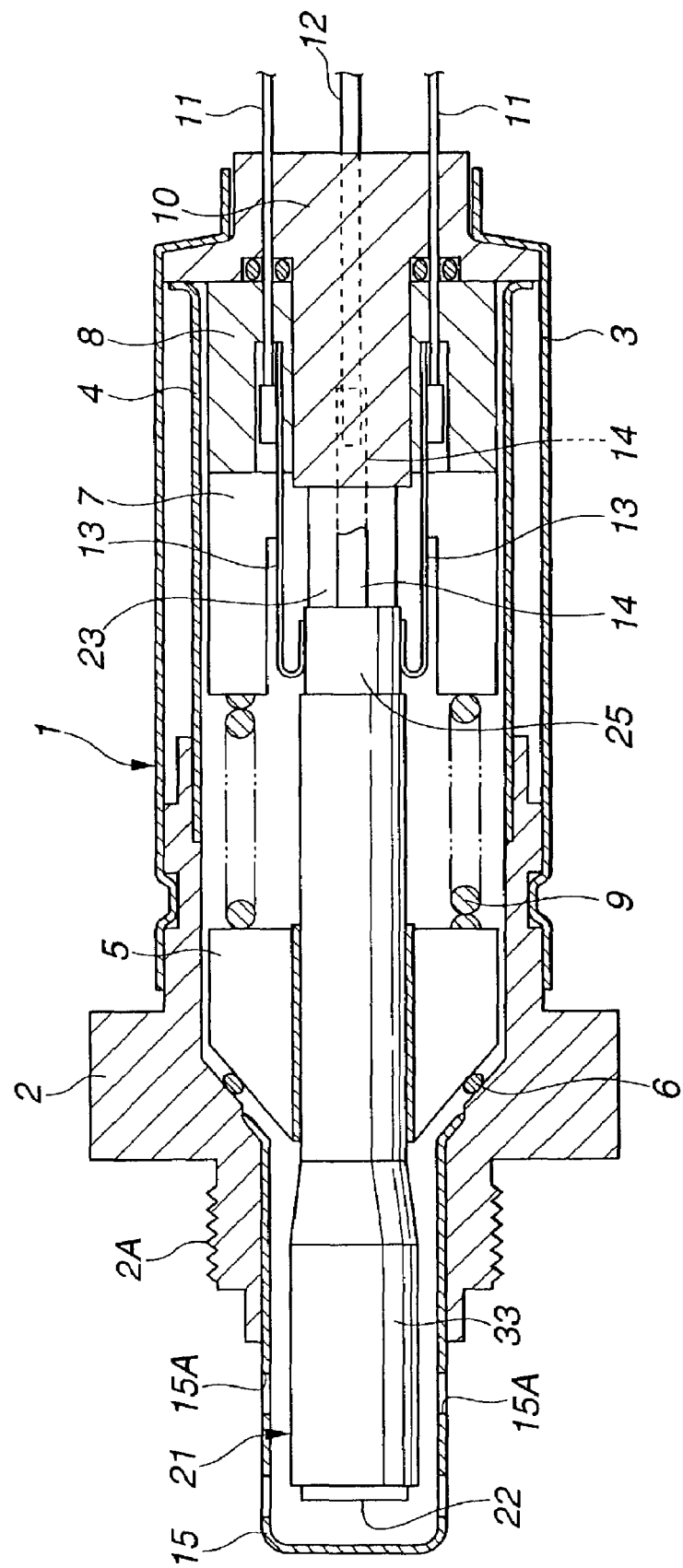
FIG. 1 is a longitudinal section showing an air/fuel ratio sensor formed with a first air/fuel ratio detection device according to a first embodiment of the present invention.

As is seen from FIG. 1, designated numeral 1 is a casing of the first air/fuel ratio sensor. This casing 1 comprises (a) cylindrical holder 2 having external threaded portion 2A, (b) cylindrical cap 3 that is integrally secured to a base portion of holder 2, and (c) guiding tube 4 that is disposed to be concentric with cap 3 and is positioned between the after-mentioned sealing cap 10 and holder 2.

Each of holder 2, cap 3 and guiding tube 4 can be made of a metal material such as stainless steel. External threaded portion 2A is threadedly engaged with an exhaust pipe such that the after-mentioned air/fuel ratio detection device 21 protrudes into the inside space of exhaust pipe.

Designated by numeral 5 is an insulating support that is disposed in a void space defined by holder 2 with an interposal of metal seal ring 6. Insulating support 5 has a generally cylindrical shape and a cylindrical opening for receiving air/fuel ratio detection device 21 and is made of a ceramic material (e.g., aluminum oxide ($Al_2O_3$)). In fact, air/fuel ratio detection device 21 is secured to the inner cylindrical wall of insulating support 5 by an inorganic bond or the like. Thus, air/fuel ratio detection device 21 is positioned at a proper position in casing 1 by insulating support 5 and is electrically and thermally insulated by insulating support 5.

Designated by numerals 7, 8 are insulating cylindrical members disposed in the inside space of guiding tube 4. Each of these cylindrical members 7, 8 is made of a ceramic material (e.g., aluminum oxide (hereinafter referred to as alumina) and keeps the after-mentioned contact plates 13, 14 and the like in an insulated condition against the casing 1.

Designated by numeral 9 is a spring (as an elastic member) that is positioned in the inside of casing 1 and is sandwiched between insulating support 5 and insulating cylindrical member 7. Spring 9 biases insulating support 5 toward holder 2 and serves to prevent a direct transmission of vibration, shock and the like from an outside to air/fuel ratio detection device 21 through casing 1.

Designated by numeral 10 is a seal cap for closing a base end of cap 3. Seal cap 10 has a stepped cylindrical shape and is made of a heat-resistant resin material (e.g., polytetrafluoroethylene (PTFE)). Insulating cylindrical members 7, 8 and the like are positioned at proper positions in the inside of casing 1 with a biasing force of spring 9.

Lead wires 11, 11 for detecting air/fuel ratio and lead wires 12, 12 (only one is shown in FIG. 1) for energizing the heater portion are inserted into the seal cap 10. Lead wires 11, 11 are electrically connected with contact plates 13, 13, and lead wires 12, 12 are electrically connected with contact plates 14, 14.

Designated by numeral 15 is a protector formed on holder 2 of casing 1. Protector 15 is formed into a cylindrical shape by using a heat-resistant metal plate or the like. Protector 15 is attached at its base portion to holder 2 to cover an end portion of air/fuel ratio detection device 21. With this, the end portion of protector 15 protrudes from holder 2 in its axial direction.

Protector 15 is formed at its end portion with a plurality of openings 15A for guiding the exhaust gas (flowing through the exhaust pipe) toward the end portion of air/fuel ratio detection device 21.

Figure 2:
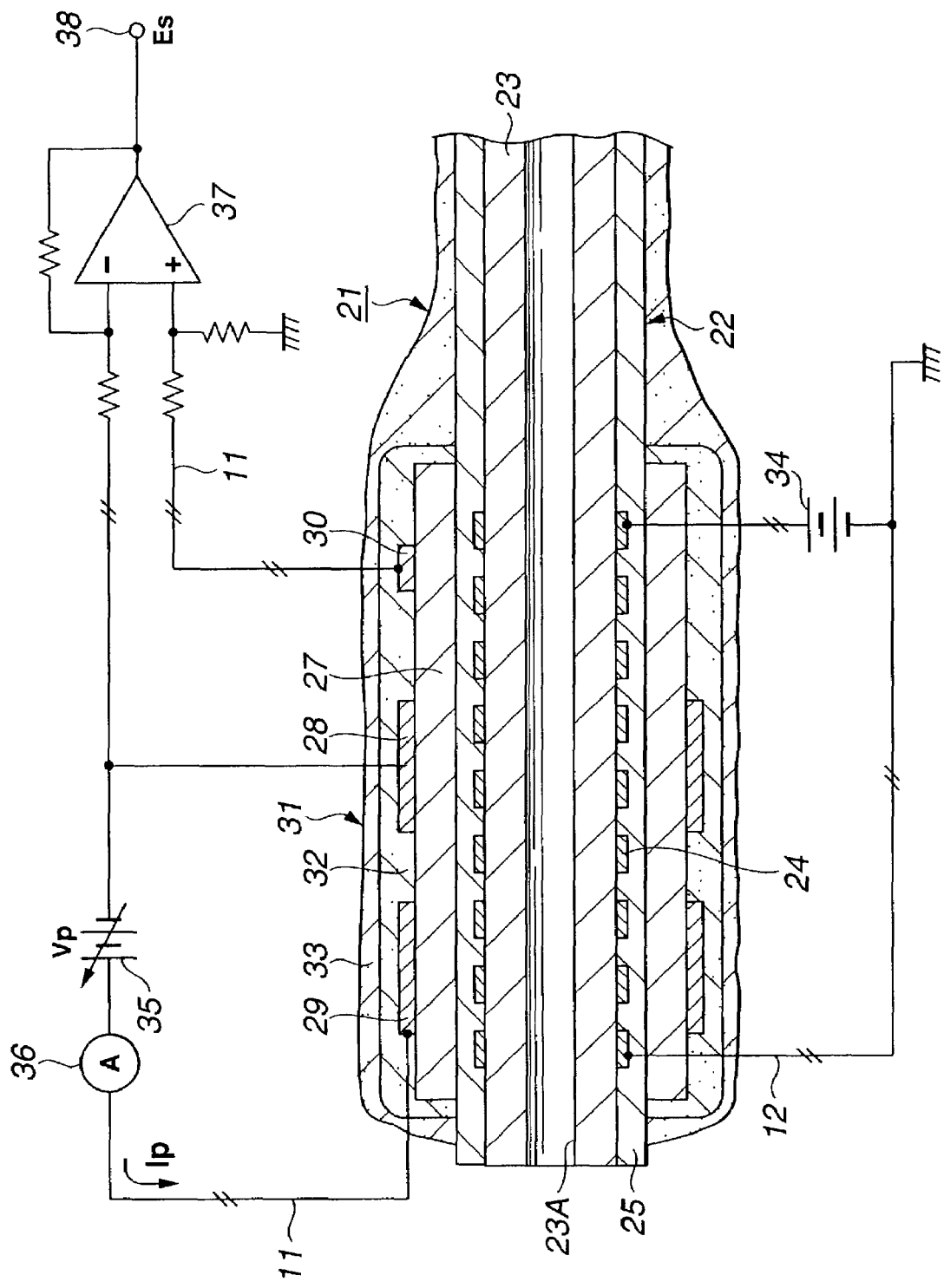
FIG. 2 is a longitudinal section showing the first air/fuel ratio detection device of FIG. 1.
Figure 7:
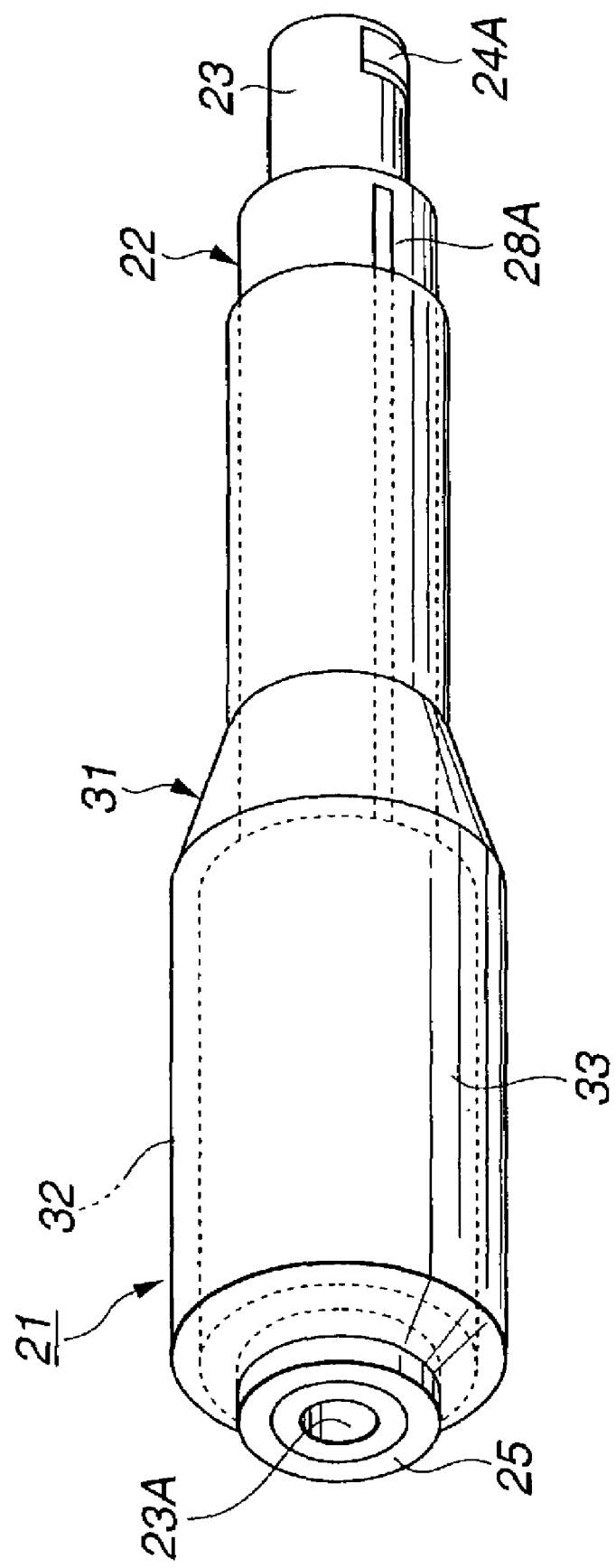
FIG. 7 is a perspective view showing the first air/fuel ratio detection device prepared by forming a second diffusion layer on a first diffusion layer by thermal spraying.

Air/fuel ratio detection device 21 is fixed in the inside of holder 2 by insulating support 5, and the end portion of device 21 protrudes from holder 2 in the axial direction. As shown in FIGS. 2 and 7, air/fuel ratio detection device 21 comprises heater portion 22, solid electrolyte layer 27 and diffusion layer 31.

Figure 3:
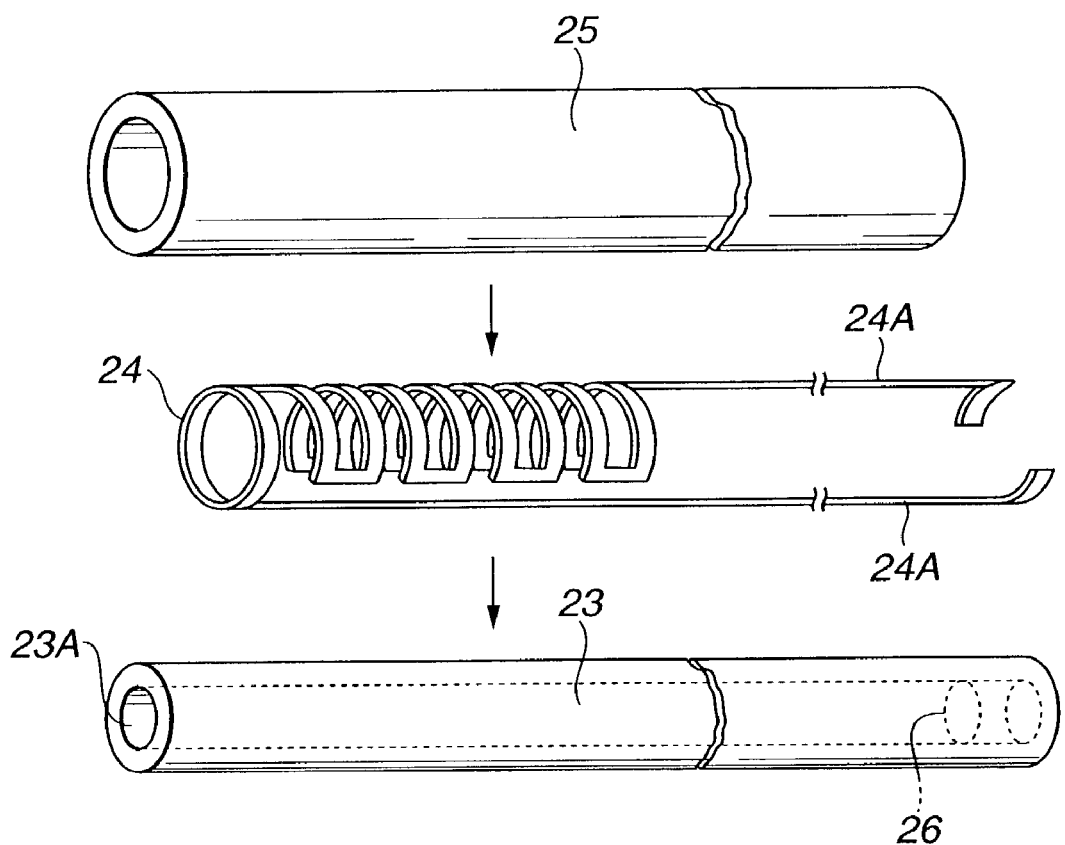
FIG. 3 is an exploded perspective view showing parts of a heater portion of the first air/fuel ratio detection device.
Figure 4:
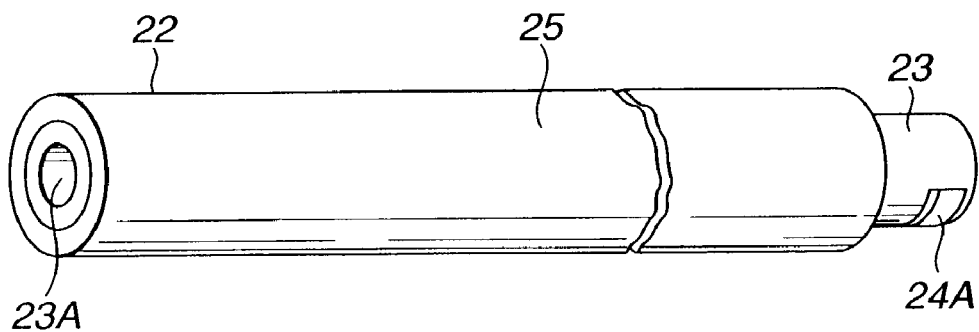
FIG. 4 is a perspective view showing the heater portion in which the parts of FIG. 3 have been assembled together.

As is seen from FIGS. 2-4, heater portion 22 (having an elongate cylindrical shape) comprises (a) core pipe 23 formed into a hollow cylindrical shape by a ceramic material (e.g., alumina), (b) heater pattern, and (c) insulating, heater covering layer 25.

As is seen from FIG. 3, heater pattern 24 is formed on the periphery of core pipe 23 by a curved surface printing or the like. Heater pattern 24 has a pair of leads 24A, 24A extending in the axial direction of core pipe 23. Heater covering layer 25 is formed on the periphery of core pipe 23 by a thick film printing using a ceramic material (e.g., alumina) for the purpose of protecting heater pattern 24 together with its leads 24a.

Core pipe 23 is formed into an elongate cylindrical shape by injection molding of a ceramic material (e.g., alumina), for example, to have an outer diameter of about 3-4 mm and an axial length of about 50-60 mm. Core pipe 23 has cylindrical hole 23A extending in the axial direction. This hole 23A reduces the volume of core pipe 23 and thereby serves to reduce heat capacity of core pipe 23.

Heater pattern 24 is made of an exothermic conductive material (e.g., platinum mixed with 10 wt % of alumina). Each lead 24A is connected at the base end portion of core pipe 23 with each contact plate 14, as shown in FIG. 1. Electricity is supplied to heater pattern 24 from the after-mentioned power source 34 through leads 12, contact plates 14 and leads 24A, thereby heating heater portion 22 at a temperature of about 650-800° C.

As is seen from FIG. 3, designated by numeral 26 is a plug. Similar to core pipe 23, plug 26 is made of a ceramic material (e.g., alumina). Plug 26 is fit into a base end of the cylindrical hole 23A to close the cylindrical hole 23A. Cylindrical hole 23A of core pipe 23 can be used as a centering hole for conducing a curved surface printing of the after-mentioned solid electrolyte layer 27, first diffusion layer 32 and the like. Thus, it is preferable in the preparation of the first air/fuel ratio sensor to carry out the sequential steps of (a) conducting a curved surface printing of solid electrolyte layer 27 and first diffusion layer 32 and the like; (b) forming plug 26 at the base end portion of cylindrical hole 23A; and (c) sintering plug 26 together with core pipe 23.

Figure 5:
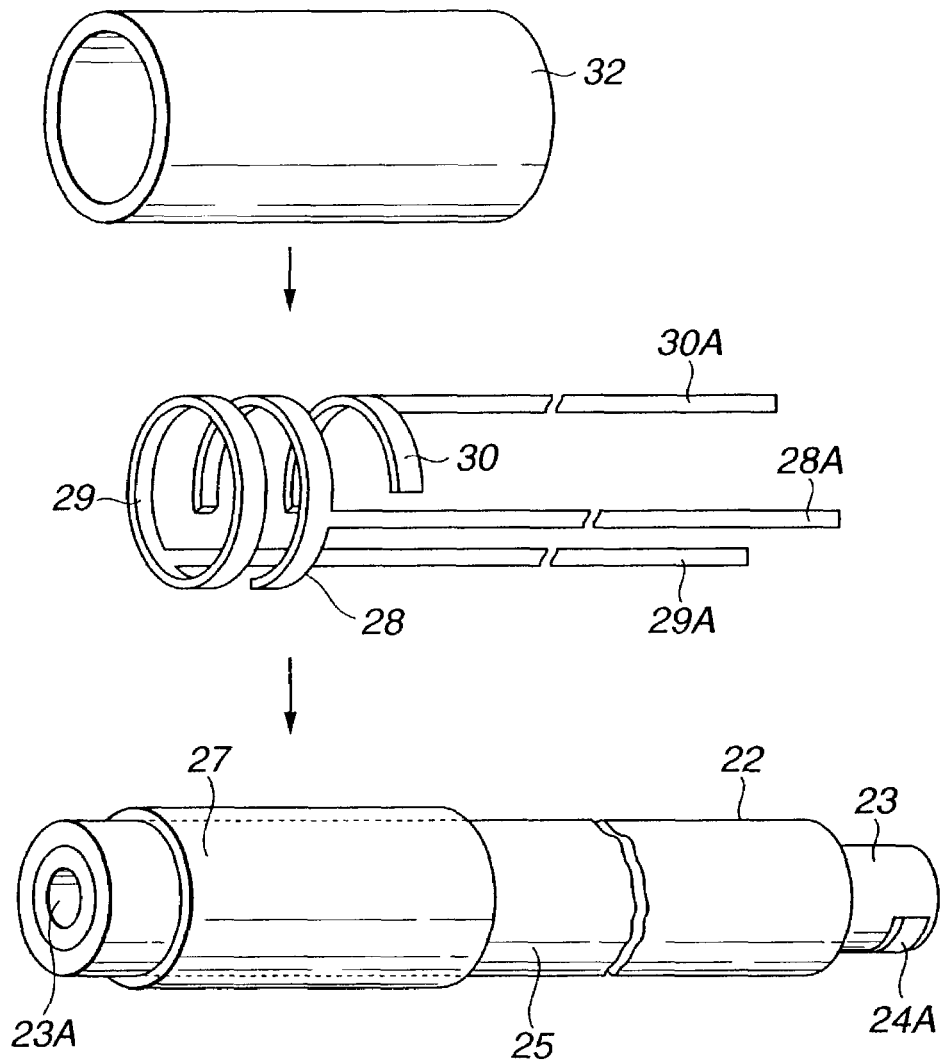
FIG. 5 is a perspective view showing further parts of the first air/fuel ratio detection device.
Figure 6:
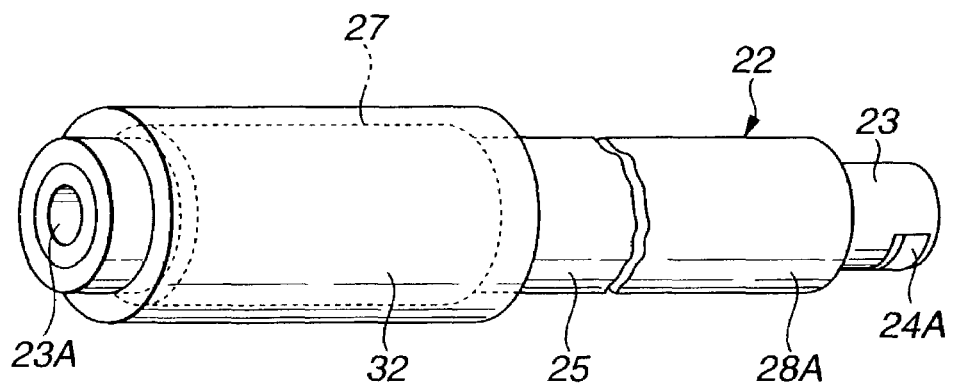
FIG. 6 is a perspective view showing a condition in which the further parts of FIG. 5 have been assembled together.

As is seen from FIG. 2, designated by numeral 27 is an oxygen ion conductive solid electrolyte layer. Solid electrolyte layer 27 is formed on the periphery of heater covering layer 25 of heater portion 22 by using a curved surface printing technique or the like. As is shown in FIG. 5, solid electrolyte layer 27 can be formed into a cylindrical shape by conducting a thick film printing of a paste on the periphery of heater covering layer 25. This paste can be made from a mixture (a so-called yttria-stabilized zirconia) of 95 mol % of a zirconia ($ZrO_2$) powder and 5 mol % of an yttria ($Y_2O_3$) powder.

Solid electrolyte layer 27 has a thickness of, for example, about 50-100 μm and transport oxygen ions therethrough between the after-mentioned first and second electrodes 28, 29. With this, solid electrolyte layer 27 generates the after-mentioned pumping electromotive force Ep. Its internal resistance Rp is defined in the after-mentioned expression.

Designated by numerals 28, 29 are respectively first and second electrodes formed on the periphery of solid electrolyte layer 27 to be away from each other. In fact, first and second electrodes 28, 29 can be formed on the periphery of solid electrolyte layer 27 and heater covering layer 25 by conducting a curved surface printing using a conductive paste of platinum or the like to have a printing pattern shown in FIG. 5. Their leads 28A, 29A extend toward the base end of the heater portion 22.

First electrode 28 becomes a cathode, at which a chemical reaction represented by the after-mentioned reaction formula (1) or (3) occurs. Second electrode 29 becomes an anode, at which a chemical reaction represented by the after-mentioned reaction formula (2) or (4) occurs. As is shown in FIG. 1, leads 28A, 29A of electrodes 28, 29 are connected at the base end side of air/fuel ratio detection device 21 with contact plates 13 and leads 11, and pumping voltage Vp is applied between electrodes 28, 29 from the after-mentioned direct voltage source 35.

Designated by numeral 30 (see FIGS. 2 and 5) is a reference electrode formed on the periphery of solid electrolyte layer 27 to be away from first and second electrodes 28, 29. Similar to first and second electrodes 28, 29, reference electrode 30 can be formed on the periphery of solid electrolyte layer 27 and heater covering layer 25 by a curved surface printing using a conductive paste of platinum or the like to have a printing pattern shown in FIG. 5. Its lead 30A extends towards the base end side of heater portion 22.

Reference electrode 30 is disposed to be away from first and second electrodes 28, 29 in the axial direction of solid electrolyte layer 27. Its lead 30A is connected at the base end side of air/fuel ratio detection device 21 with contact plate 13 and lead 11, which are different from those connected with leads 28A, 29A. Reference electrode 30 and first electrode 28 are connected with the after-mentioned differential amplifier 37 (see FIG. 2).

Designated by numeral 31 is a diffusion layer made of a porous material and covering solid electrolyte layer 27 and electrodes 28-30 from outside. As is seen from FIGS. 2 and 7, diffusion layer 31 comprises (a) a first diffusion layer 32 formed on the periphery of solid electrolyte layer 27 by a curved surface printing or the like and (b) the after-mentioned second diffusion layer 33.

First diffusion layer 32 can be formed into a cylindrical shape to have a thickness, for example, of about 30-100 μm by conducting a thick film printing in which a paste (for example, containing alumina powder) is applied to the periphery of solid electrolyte layer 27. Alternatively, this paste can be prepared by mixing alumina powder with a small amount of zirconia powder.

First diffusion layer 32, as well as second diffusion layer 33, has a porous structure and thereby has a function of transmitting a part of the exhaust gas (flowing around second diffusion layer 33) towards electrodes 28-30. In this case, first diffusion layer 32 has a higher porosity or coarser structure as compared with second diffusion layer 33.

Second diffusion layer 33 is formed on outside of first diffusion layer 32. In fact, as is shown in FIG. 7, second diffusion layer 33 can be formed by plasma spraying to cover the periphery of first diffusion layer 32 and heater covering layer 25 using a porous ceramic material, for example, of a mixture of magnesium oxide and aluminum oxide.

Second diffusion layer 33 (having a thickness, for example, of 100 μm or less) covers first diffusion layer 32, thereby providing a space for adjusting the after-mentioned pumping current Ip. Furthermore, second diffusion layer 33 covers heater covering layer 25 of heater portion 22, thereby protecting leads 28A, 29A and 30A of electrodes 28-30. Second diffusion layer 33 has a finer porous structure than that of first diffusion layer 32.

Designated by numeral 34 is a heater power source provided outside of casing 1. As is shown in FIG. 2, heater power source 34 is connected with heater pattern 24 through lead 12 and the like. Heater power source 34 heats heater portion 22 at a temperature of about 650-800° C. by applying voltage to heater pattern 24 of heater portion 22.

Designated by numeral 35 is a direct current power source provided outside of casing 1. As is shown in FIG. 2, direct current power source 35 is connected with first and second electrodes 28, 29 through lead 11, thereby applying pumping voltage Vp between first electrode (cathode) and second electrode (anode). Pumping voltage Vp of direct current power source 35 may be kept at a constant voltage (e.g., about 0.6 V) or varied according to need.

Designated by numeral 36 is an ammeter disposed between and connected with direct current power source 35 and second electrode 29. Ammeter 36 detects pumping current Ip (diffusion limiting current) flowing between first and second electrodes 28, 29.

Figure 10:
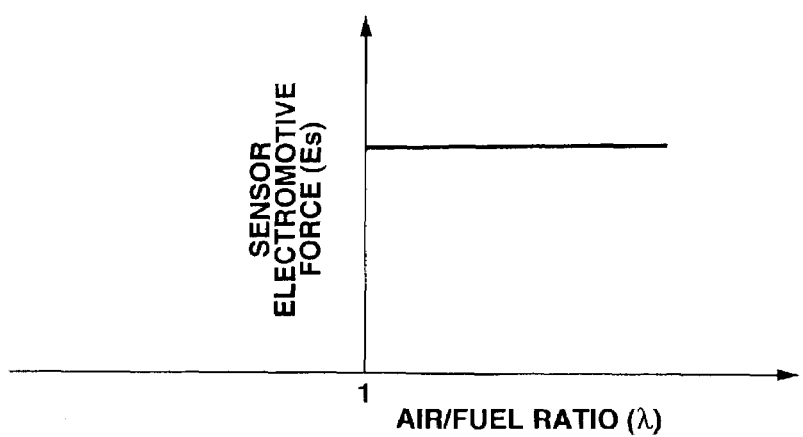
FIG. 10 is a characteristic diagram showing a relationship between air/fuel ratio (λ) and sensor electromotive force under a lean air/fuel ratio condition.
Figure 13:
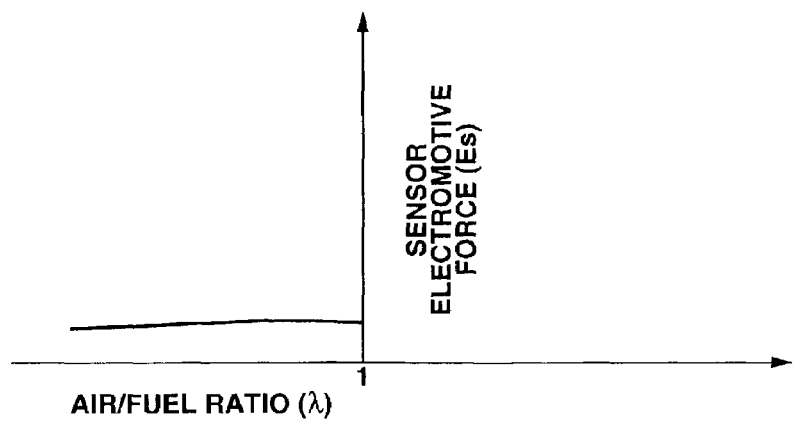
Figure 14:
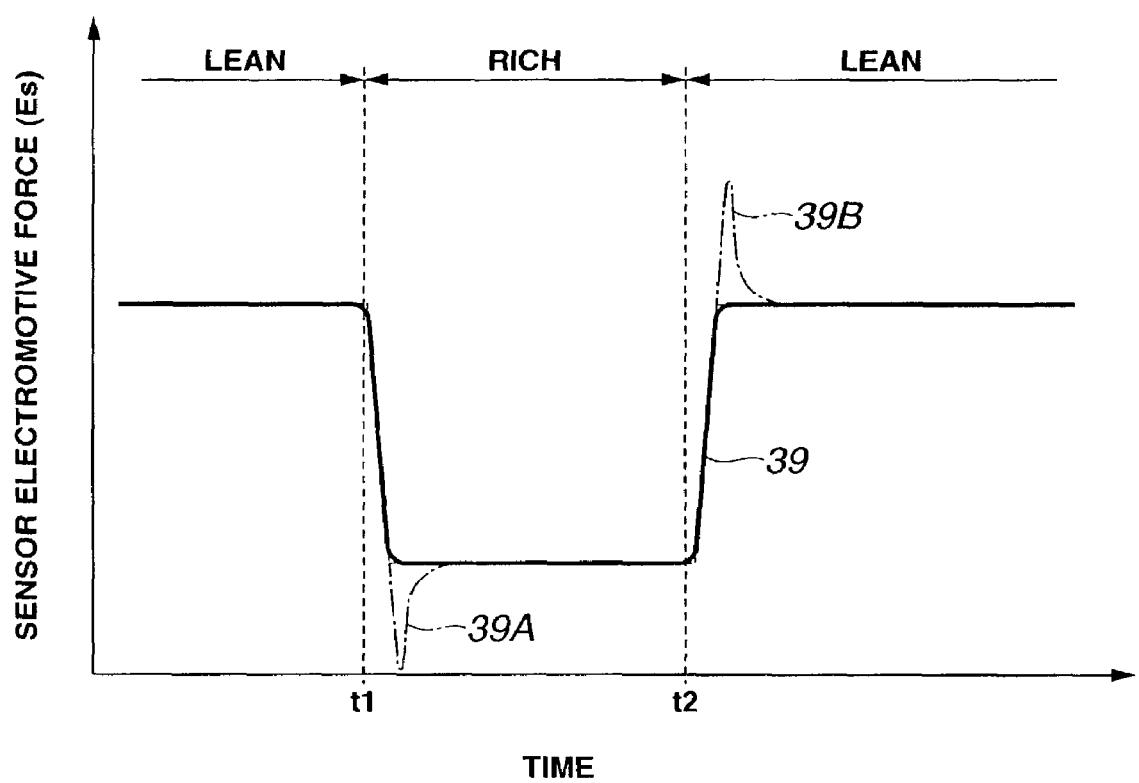
FIG. 14 is a characteristic diagram showing sensor electromotive force changes from lean condition to rich condition and vice versa.

Designated by numeral 37 is a differential amplifier that is provided outside of casing 1 and constitutes a part of an air/fuel ratio detection circuit. As is seen from FIG. 2, its non-inverting input terminal is connected with reference electrode 30 through lead 11, and inverting input terminal is connected with first electrode 28. As is shown in FIGS. 10, 13 and 14, differential amplifier 37 outputs sensor electromotive force Es (air/fuel ratio detection signal) from its output terminal 38.

With reference to FIGS. 3 to 7, the method for producing air/fuel ratio detection device 21 will be explained in the following.

For producing heater portion 22, a ceramic material (e.g., alumina) is formed into a hollow cylindrical rod as core pipe 23 by injection molding, followed by preliminary sintering. In this case, it is preferable to enlarge the diameter of cylindrical hole 23A as large as possible in order to reduce heat capacity of core pipe 23.

In the pattern-printing step, a supporting shaft (e.g., chuck) is engaged with both ends of cylindrical hole 23 to rotate core pipe 23. While core pipe 23 is rotated, an exothermic conductive material (e.g., platinum mixed with 10 wt % alumina) is applied to the periphery of core pipe 23 by curved surface printing to form heater pattern 24. Furthermore, each lead 24A of heater pattern 24 is printed to extend toward the base end of core pipe 23, thereby making heater pattern have a one-piece construction.

Then, heater covering layer 25 for covering heater pattern 24 is formed by conducting a curved surface printing using a paste (e.g., alumina) or by putting a ceramic green sheet (e.g., of alumina) on the outside of core pipe 23. With this, there is provided heater portion 22 formed of core pipe 23, heater pattern 24 and heater covering layer 25, as shown in FIG. 4.

Then, as shown in FIG. 5, oxygen ion conductive solid electrolyte layer 27 is formed by conducting a curved surface printing of a paste (e.g., containing a mixture of zirconia and yttria) on the periphery of heater covering layer 25.

Then, electrodes 28-30 are formed by conducting a curved surface printing of a conductive paste (e.g., of platinum) on the peripheral surface of solid electrolyte layer 27 such that electrodes 28-30 are away from each other in the axial direction of solid electrolyte layer 27. Furthermore, leads 28A, 29A and 30A are formed by printing such that these leads extend toward the base end of heater covering layer 25 while they are away from each other.

Then, as shown in FIG. 5, first diffusion layer 32 is formed by conducting a curved surface printing of a paste (e.g., of alumina or of an alumina containing zirconia) on the periphery of solid electrolyte layer 27.

Then, an assembly of core pipe 23, heater pattern 24, heater covering layer 25, solid electrolyte layer 27, electrodes 28-30, and first diffusion layer 32 is subjected to a sintering for about 2 hr at a high temperature, for example, of about 1,300-1,500° C. With this, the sintered assembly is made to have a one-piece construction. Furthermore, it is preferable to form plug 26 (shown in FIG. 3) in cylindrical hole 23A of core pipe 23 prior to sintering, and then to conduct its sintering together with the above-mentioned members.

Then, second diffusion layer 33 is formed by plasma spraying of a ceramic material (e.g., an alumina containing magnesium oxide) on the sintered assembly to fully cover first diffusion layer 32 and heater covering layer 25.

Upon conducting plasma spraying, thickness of second diffusion layer 33 is suitably adjusted. With this, it is possible to prevent variation of the after-mentioned pumping current Ip among products and to easily conduct the adjustment of gas diffusion resistance even after sintering of the assembly.

As is shown in FIG. 1, the thus produced air/fuel ratio detection device 21 is put into casing 1 in a manner to bring leads 24A, 28A, 29A and 30A into contact with respective contact plates 13, 14, thereby completing air/fuel ratio sensor.

Operation of air/fuel detection sensor will be described as follows. Casing 1 is threadedly secured to a vehicular exhaust pipe through external threaded portion 2A such that an end portion of air/fuel ratio detection device 21 protrudes into the inside space of the exhaust pipe.

Then, an exhaust gas flowing through the exhaust pipe reaches surroundings of air/fuel ratio detection device 21 through protector 15 by starting engine, and a part of this exhaust gas is transmitted through second diffusion layer 33 and first diffusion layer 32 and then reaches the surface of electrodes 28, 29.

Air/fuel ratio detection device 21 is heated by heater portion 22 as electricity is supplied from heater power source 34 to heater pattern 24. With this, solid electrolyte layer 27 is activated, and thereby diffusion limiting current (pumping current Ip) is allowed to flow between first electrode (cathode) 28 and second electrode (anode) 29, in accordance with the oxygen concentration of the exhaust gas or combustible gas components concentration, as shown by the after-mentioned reaction formulas (1)-(6) and expressions (1), (3) and (4).

In fact, when air/fuel ratio is greater than stoichiometric air/fuel ratio ($\lambda=1$), air/fuel mixture is in a lean-burn condition. With this, the unburned oxygen remains in the exhaust gas flowing through surroundings of diffusion layer 31.

Therefore, the chemical reaction represented by the following reaction formula (1) occurs at electrode 28 under a condition that pumping voltage Vp is applied between electrodes 28, 29. With this, oxygen ions are generated as electrons are added to molecular oxygen remaining in the exhaust gas.

$$O_2 + 4e(\text{electron}) \rightarrow 2O^{2-} \qquad (1)$$

Then, the oxygen ions are transported from electrode (cathode) 28 toward electrode (anode) 29 through oxygen defects of solid electrolyte layer 27. Then, the oxygen ions are decomposed into oxygen and electrons at electrode 29, as shown in the following reaction formula (2).

$$2O^{2-} \rightarrow O_2 + 4e(\text{electron}) \qquad (2)$$

Thus, pumping current Ip (diffusion limiting current) is allowed to flow between electrodes 28, 29 in accordance with the following expression (1):

$$Ip = D_0 \times \frac{4 \times F}{R \times T} \times (S1/h1) \times (Px1 - Px2) \qquad (1)$$

where Do represents oxygen gas diffusion coefficient of diffusion layer 31; Px1 represents oxygen partial pressure of detection gas (e.g., oxygen partial pressure at reference electrode 30); Px2 represents oxygen partial pressure on cathode (electrode 28) side; R represents gas constant (8.3145 J/K·mol); T represents absolute temperature; F represents Faraday constant (9.64853×10⁴ C/mol); S1 represents area of diffusion layer 31 on cathode side; and h1 represents thickness of diffusion layer 31 on cathode side.

When resistance (i.e., internal resistance of solid electrolyte layer 27) between electrodes 28, 29 is designated by "Rp", the following expression (2) is satisfied.

$$Vp = Ep + (Ip \times Rp) \qquad (2)$$

wherein Vp is pumping voltage supplied by direct current power source 35; Ep is pumping electromotive force occurring in solid electrolyte layer 27; and Ip is pumping current.

Figure 8:
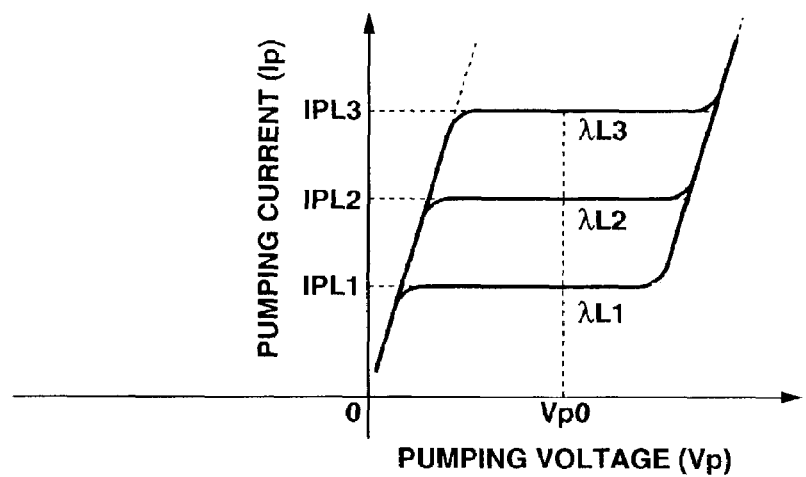
FIG. 8 is a characteristic diagram showing a relationship between pumping voltage (Vp) and pumping current (Ip) under a lean air/fuel ratio condition.

As shown in FIG. 8, it is possible to examine the change of pumping current with ammeter 36 by gradually increasing pumping voltage Vp of direct current power source 35 from 0V under lean-burn conditions having air/fuel ratios of $\lambda L1$, $\lambda L2$ and $\lambda L3$ ($1<\lambda L1<\lambda L2<\lambda L3$). With this, as is shown in FIG. 8, it was confirmed that pumping current Ip reaches diffusion limit at a current of IPL1 when air/fuel ratio is $\lambda L1$, that it reaches diffusion limit at IPL2 when air/fuel ratio is λL2, and that it reaches diffusion limit at IPL3 when air/fuel ratio is λL3.

Thus, the relationship between air/fuel ratio λ and pumping current Ip can be represented by a linear characteristic line (shown in FIG. 9) by maintaining voltage Vpo (see FIG. 8) at a constant level (e.g., about 0.6V).

Figure 9:
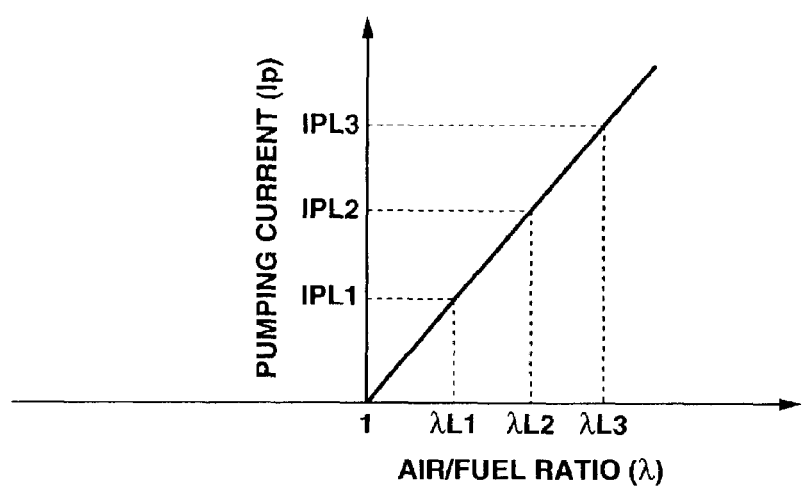
FIG. 9 is a characteristic diagram showing a relationship between air/fuel ratio (λ) and pumping current (Ip) under a lean air/fuel ratio condition.

Therefore, as is shown in FIG. 9, it is possible to determine air/fuel ratio by detecting pumping current Ip using ammeter 36 under a condition that pumping voltage Vp is kept at constant voltage Vpo. For example, air/fuel ratio is found to be λL1 when pumping current IPL1 is detected.

Furthermore, it is possible to output sensor electromotive force (Es) (represented by a characteristic line shown in FIG. 10) as an air/fuel ratio detection signal under a lean-burn condition, from output terminal 38 of differential amplifier 37 shown in FIG. 2.

The case of rich fuel condition, in which air/fuel ratio of engine is less than stoichiometric air/fuel ratio (λ=1), will be explained in detail in the following. In this case, oxygen does not remain in the exhaust gas flowing through surroundings of diffusion layer 31. In other words, combustible gas components, (e.g., carbon monoxide (CO) and hydrogen ($H_2$)) remain in the exhaust gas by incomplete combustion. The case of carbon monoxide will be explained in detail in the following.

The chemical reaction, represented by the following reaction formula (3), occurs at electrode (cathode) 28 by applying pumping voltage Vp between electrodes 28, 29. With this, electrons are added to carbon dioxide remaining in the exhaust gas, thereby generating oxygen ions and carbon monoxide.

$$2CO_2 + 4e(\text{electron}) \rightarrow 2O^{2-} + 2CO \qquad (3)$$

Then, oxygen ions are transported from electrode (cathode) 28 toward electrode (anode) 29 through oxygen defects of solid electrolyte layer 27.

The thus transported oxygen ions are reacted with carbon monoxide at electrode 29, thereby generating carbon dioxide and electrons, as shown by the following reaction formula (4).

$$2CO + 2O^{2-} \rightarrow +2CO_2 + 4e \qquad (4)$$

Thus, pumping current Ip (diffusion limiting current) is allowed to flow between electrodes 28, 29 in accordance with the following expression (3):

$$Ip = D_{CO} \times \frac{4 \times F}{R \times T} \times (S2/h2) \times (Px3 - Px4) \qquad (3)$$

where Dco represents carbon monoxide gas diffusion coefficient of diffusion layer 31; Px3 represents carbon monoxide partial pressure of detection gas (e.g., carbon monoxide partial pressure at reference electrode 30); Px4 represents carbon monoxide partial pressure on anode (electrode 29) side; S2 represents area of diffusion layer 31 on anode side; and h2 represents thickness of diffusion layer 31 on anode side.

In the case of hydrogen (as a combustible gas component in the exhaust gas), the chemical reaction, represented by the following reaction formula (5), occurs at electrode (cathode) 28. With this, electrons are added to water molecule remaining in the exhaust gas, thereby generating oxygen ions and hydrogen molecules.

$$2H_2O + 4e(\text{electron}) \rightarrow 2O^{2-} + 2H_2 \qquad (5)$$

Then, oxygen ions are transported from electrode (cathode) 28 toward electrode (anode) 29 through oxygen defects of solid electrolyte layer 27.

The thus transported oxygen ions are reacted with hydrogen molecule (existing in the exhaust gas) at electrode 29, thereby generating water molecules and electrons, as shown by the following reaction formula (6).

$$2H_2 + 2O^{2-} \rightarrow +2H_2O + 4e \qquad (6)$$

Thus, pumping current Ip (diffusion limiting current) is allowed to flow between electrodes 28, 29 in accordance with the following expression (4):

$$Ip = DH \times \frac{4 \times F}{R \times T} \times (S2/h2) \times (Px5 - Px6) \qquad (4)$$

where $D_H$ represents hydrogen gas diffusion coefficient of diffusion layer 31; Px5 represents hydrogen partial pressure of detection gas (e.g., hydrogen partial pressure at reference electrode 30); and Px6 represents hydrogen partial pressure on anode (electrode 29) side.

Even if air/fuel ratio is in a rich condition (λ<1), the relationship shown in the above expression (2) is satisfied.

Figure 11:
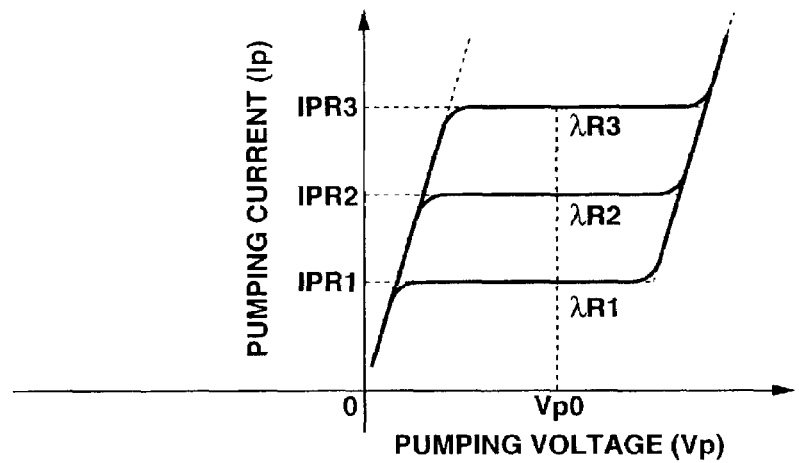
FIGS. 11-13 are characteristic diagrams respectively similar to those of FIGS. 8-10, but under a rich air/fuel ratio condition.

As shown in FIG. 11, it is possible to examine the change of pumping current with ammeter 36 by gradually increasing pumping voltage Vp of direct current power source 35 from 0V under rich conditions having air/fuel ratios of λR1, λR2 and λR3 (1>λR1>λR2>λR3). With this, as is shown in FIG. 11, it was confirmed that pumping current Ip reaches diffusion limit at a current of IPR1 when air/fuel ratio is λR1, that it reaches diffusion limit at IPR2 when air/fuel ratio is λR2, and that it reaches diffusion limit at IPR3 when air/fuel ratio is λR3.

Thus, the relationship between air/fuel ratio λ and pumping current Ip can be represented by a linear characteristic line (shown in FIG. 12) by maintaining voltage Vpo (see FIG. 11) at a constant level (e.g., about 0.6V).

Figure 12:
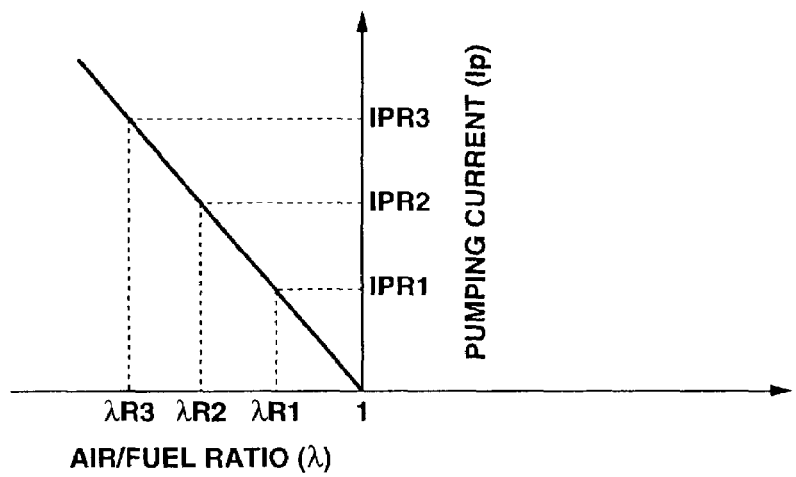

Therefore, as is shown in FIG. 12, it is possible to determine air/fuel ratio by detecting pumping current Ip using ammeter 36 under a condition that pumping voltage Vp is kept at constant voltage Vpo. For example, air/fuel ratio is found to be λR1 when pumping current IPR1 is detected.

Furthermore, it is possible to output sensor electromotive force (Es) (represented by a characteristic line shown in FIG. 13) as an air/fuel ratio detection signal under a rich condition, from output terminal 38 of differential amplifier 37 shown in FIG. 2.

It is understood from FIGS. 10 and 13 that it is possible to obtain a characteristic line 39 (represented by the continuous line of FIG. 14) of sensor electromotive force Es as an air/fuel ratio detection signal outputted from output terminal 38 of differential amplifier 37. Therefore, it is possible by this sensor electromotive force Es to detect that it is in lean-burn condition until time t1, that it is in rich condition from t1 to t2, and that it is again in lean-burn condition from t2.

There may occur overshoot of sensor electromotive force Es as shown by characteristic lines (chain lines) 39A and 39B of FIG. 14, when air/fuel ratio turns from lean-burn condition to rich condition and vice versa.

In view of such overshoot problem, according to the present invention, reference electrode 30 (formed on the periphery of solid electrolyte layer 27), together with first and second electrodes 28, 29, is covered with diffusion layer 31, and second diffusion layer 33 is formed by plasma spraying or the like such that the thickness of second diffusion layer 33 can suitably be adjusted. With this, it is possible to substantially suppress the occurrence of overshoot of sensor electromotive force Es (as shown by characteristic lines 39A and 39B of FIG. 14), thereby obtaining a stable output of Es as shown by characteristic line (continuous line) 39 of FIG. 14.

As stated above, an assembly of core pipe 23, heater pattern 24, heater covering layer 25, solid electrolyte layer 27, electrodes 28-30, and first diffusion layer 32 is subjected to a sintering in the preparation of air/fuel ratio detection device 21. Sintering condition of the sintered assemblies may be different among them. With this, gas diffusion resistance of electrodes 28, 29 tends to vary, thereby making pumping current Ip (flowing between electrodes 28, 29) inconstant or unequal among products (air/fuel ratio detection apparatuses). In view of this problem, according to the present invention, the thickness of second diffusion layer is suitably adjusted upon conducting plasma spraying to form second diffusion layer. The thus adjusted thickness may be 100 μm or less.

In fact, it is possible to examine the sintered assembly with respect to pumping current (Ip) characteristic. Based on the data of this examination, it is possible to suitably adjust the thickness of second diffusion layer 33 upon conducting plasma spraying of a ceramic material (e.g., an alumina containing magnesium oxide) on the sintered assembly. With this adjustment, it is possible to adjust gas diffusion resistance for each of electrodes 28-30 of each sintered assembly produced, thereby preventing undesirable variation (deviation) of pumping current Ip among the produced air/fuel ratio detection apparatuses.

As stated above, heater portion 22 is fully covered with solid electrolyte layer 27 and diffusion layer 31. With this, heater portion 22 is prevented from a direct contact with the outside air. Therefore, it is possible to efficiently transmit heat from heater portion to solid electrolyte layer and the like.

As stated above, first and second electrodes 28, 29 and reference electrode 30 are formed on the periphery of solid electrolyte layer 30 to be away from each other in the axial direction. With this, it is possible to reduce the diameter of air/fuel ratio detection device 21, thereby making air/fuel ratio detection apparatus smaller in size.

With reference to FIGS. 15-20, a second air/fuel ratio detection apparatus (second air/fuel ratio or oxygen sensor) according to a second embodiment of the present invention will be described in detail in the following. The second air/fuel ratio sensor is similar to the first air/fuel ratio sensor except in that first and second electrodes are opposed to each other in a radial direction of solid electrolyte layer. Explanations of parts of the second air/fuel ratio sensor, corresponding to those of the first air/fuel ratio sensor, may not be repeated hereinafter.

Figure 15:
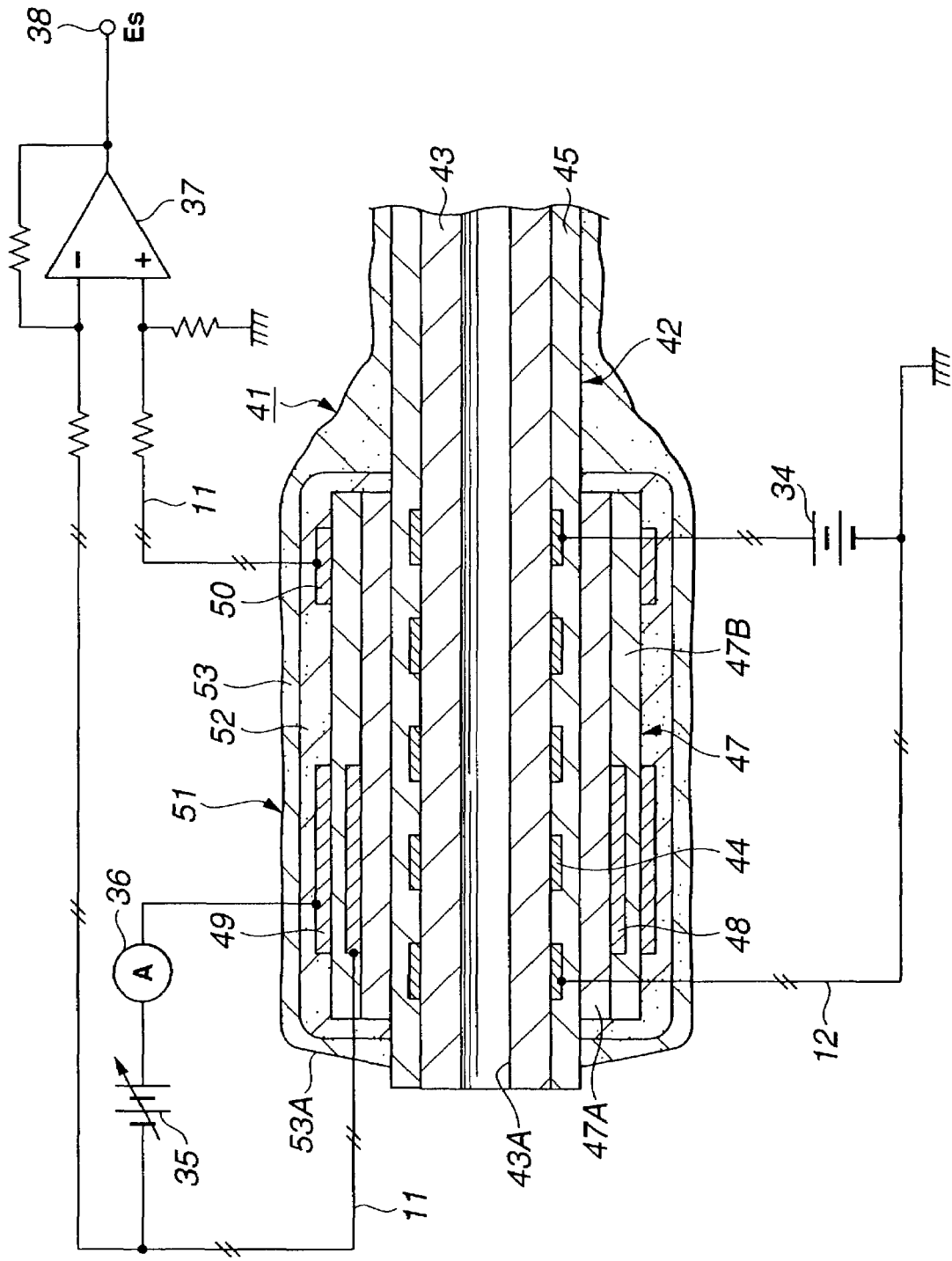
FIG. 15 is a view similar to FIG. 2, but showing a second air/fuel detection device according to a second embodiment of the present invention.

As is seen from FIG. 15, designated by numeral 41 is an air/fuel ratio detection device formed of the after-mentioned heater portion 42, solid electrolyte layer 47 and diffusion layer 51.

Figure 16:
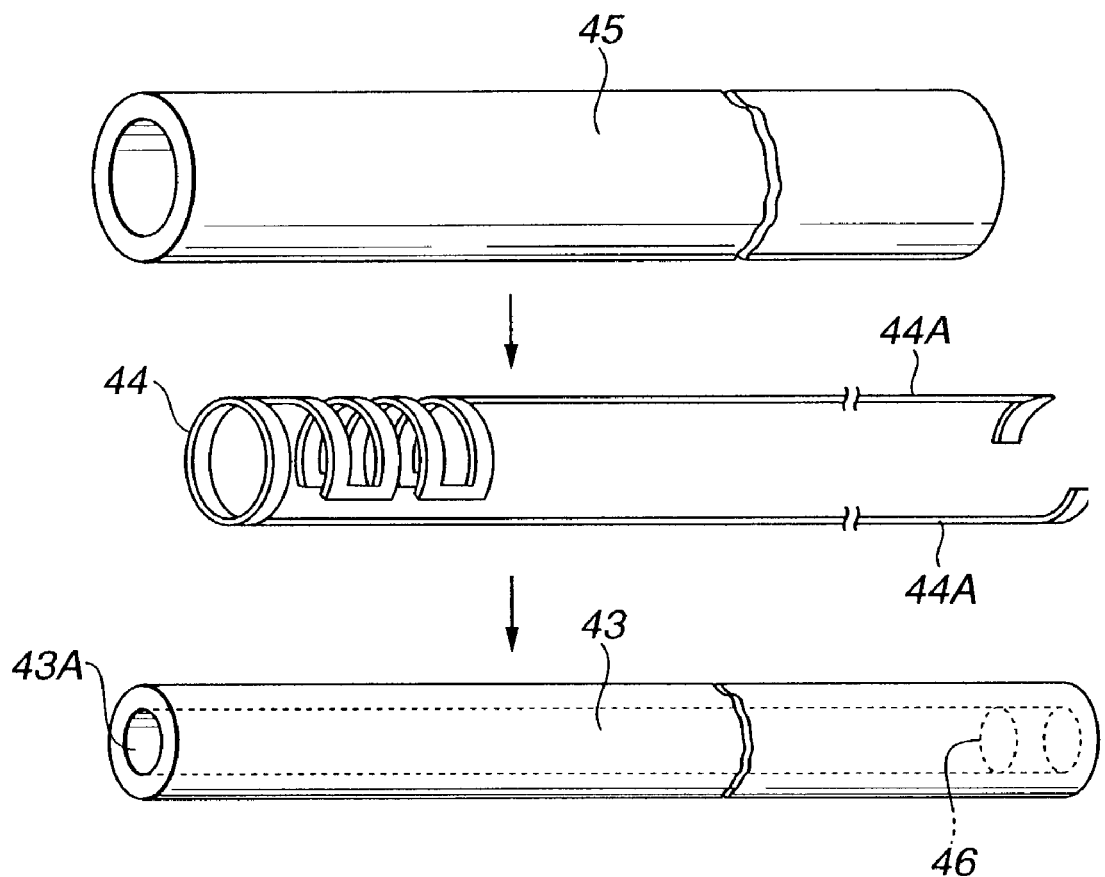
FIGS. 16-20 are views respectively similar to FIGS. 3-7, but showing those of the second air/fuel ratio detection device.

Heater portion 42 (having an elongate cylindrical shape) comprises (a) core pipe 43 (as a heater core) having a cylindrical hole 43A, (b) heater pattern 44 having a lead 44A, (c) insulating, heater covering layer 45, and (d) plug 46 (see FIG. 16).

Figure 18:
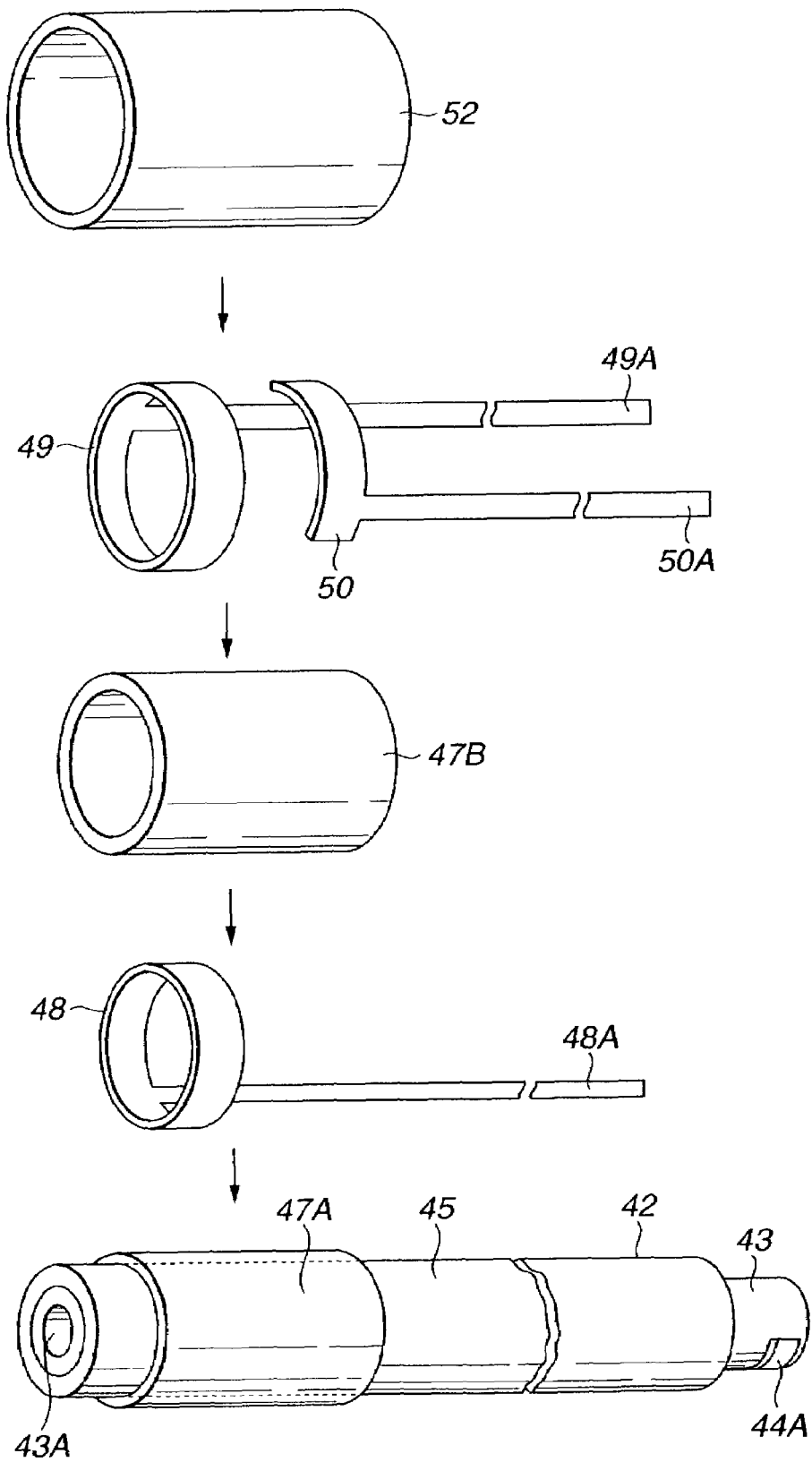
Figure 19:
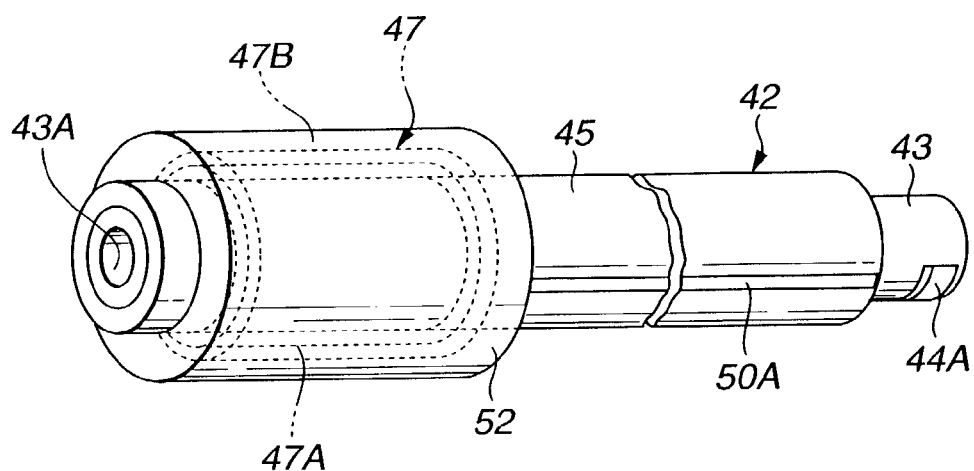

Designated by numeral 47 is an oxygen ion conductive solid electrolyte layer. Solid electrolyte layer 47 is formed on the periphery of heater covering layer 45 by using a curved surface printing technique or the like. As is shown in FIGS. 15 and 18, solid electrolyte layer 47 can be formed into a cylindrical shape by conducting a thick film printing of a paste on the periphery of heater covering layer 45. This paste can also be made by using yttria-stabilized zirconia.

Solid electrolyte layer 47 has a two-layer structure of an inner electrolyte layer 47A and outer electrolyte layer 47B. The axial length of solid electrolyte layer 47 (see FIG. 15) is substantially shorter than that of solid electrolyte layer 27 (see FIG. 2), due to the above-mentioned special configuration of the first and second electrodes.

In fact, inner electrolyte layer 47A is formed on the periphery of heater covering layer 45 of heater portion 42 by a curved surface printing or the like. Outer electrolyte layer 47B is formed on inner electrolyte layer 47A by a curved surface printing or the like to cover the after-mentioned inner electrode 48.

Inner electrode (first electrode) 48 and outer electrode (second electrode) 49 are respectively formed on the peripheries of inner and outer electrolyte layers 47A and 47B by curved surface printing or the like.

These inner and outer electrodes 48, 49 are similar to first and second electrodes 28, 29, except in that inner and outer electrodes 48, 49 are configured to sandwich outer electrode layer 47B therebetween in the radial direction.

As is seen from FIG. 18, these electrodes 48, 49 respectively have leads 48A, 49A extending toward the base end of heater portion 42. Inner electrode 48 serves as a cathode, at which the above-mentioned chemical reactions represented by the formulas (1) and (3) occur, and outer electrode 49 serves as an anode, at which the above-mentioned chemical reactions represented by the formulas (2) and (4) occur.

Designated by numeral 50 is reference electrode formed on the periphery of outer electrolyte layer 47B by a curved surface printing using a conductive paste of platinum or the like to have printing pattern shown in FIG. 18. Its lead 50A extends towards the base end of heater portion 42.

Reference electrode 50 is disposed to be away from outer electrode 49 in the axial direction of outer electrolyte layer 47B. Similar to reference electrode 30, reference electrode 50 is connected with differential amplifier 37, as shown in FIG. 15.

Designated by numeral 51 is a diffusion layer made of a porous material and covering solid electrolyte layer 47 and electrodes 49, 50 from outside. Similar to diffusion layer 31, diffusion layer 51 also comprises first and second diffusion layers 52, 53, as is seen from FIGS. 15 and 20.

With reference to FIGS. 16 to 20, the method for producing air/fuel ratio detection device 41 will be explained in the following.

For producing heater portion 42, a ceramic material (e.g., alumina) is formed into a hollow cylindrical rod as core pipe 43 by injection molding, followed by preliminary sintering.

In the pattern-printing step, a supporting shaft (e.g., chuck) is engaged with both ends of cylindrical hole 43A to rotate core pipe 43. While core pipe 43 is rotated, an exothermic conductive material (e.g., platinum or tungsten) is applied to the periphery of core pipe 43 by curved surface printing to form heater pattern 44.

Figure 17:
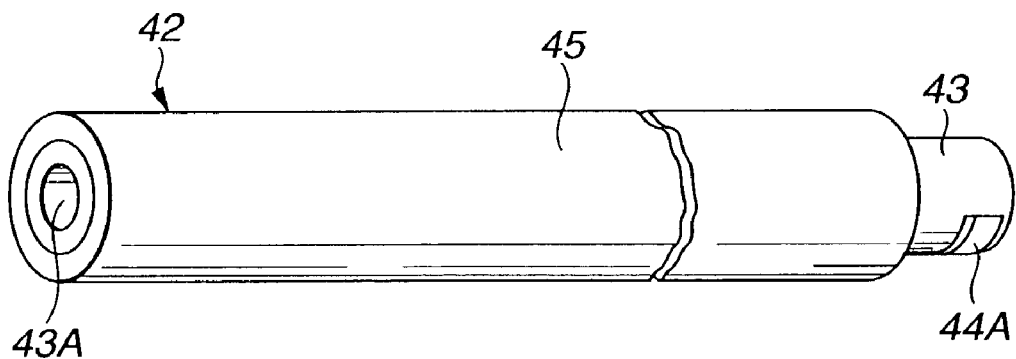

Then, similar to the first embodiment, heater covering layer 45 can be formed by conducting a curved surface printing using a paste (e.g., alumina) or by putting a ceramic green sheet on the outside of core pipe 43. With this, there is provided heater portion 42 formed of core pipe 43, heater pattern 44 and heater covering layer 45, as shown in FIG. 17.

Then, as shown in FIG. 18, oxygen ion conductive inner electrolyte layer 47A is formed by conducting a curved surface printing of a paste (e.g., containing a mixture of zirconia and yttria) on the periphery of heater covering layer 45.

Then, inner electrode 48 is formed by conducting a curved surface printing of a conductive paste (e.g., of platinum) on the peripheral surface of inner electrolyte layer 47A. Furthermore, lead 48A is formed by printing such that it extends toward the base end of heater covering layer 45.

Then, oxygen ion conductive outer electrolyte layer 47B is formed by conducting a curved surface printing of a paste (e.g., of zirconia and yttria) on the peripheral surface of inner electrolyte layer 47A.

Then, outer electrode 49 and reference electrode 50 are formed by conducting a curved surface printing of a conductive paste (e.g., of platinum) on the peripheral surface of outer electrolyte layer 47B such that electrodes 49, 50 are away from each other in the axial direction of outer electrolyte layer 47B. Furthermore, their respective leads 49A, 50A are formed by printing such that these leads extend toward the base end of heater covering layer 45 while they are away from each other.

Then, as shown in FIG. 18, first diffusion layer 52 is formed by conducting a curved surface printing of a paste (e.g., of alumina or of alumina containing zirconia) on the periphery of outer electrolyte layer 47B.

Then, similar to the first embodiment, an assembly of core pipe 43, heater pattern 44, heater covering layer 45, solid electrolyte layer 47, electrodes 48-50, and first diffusion layer 52 is subjected to a sintering.

Figure 20:
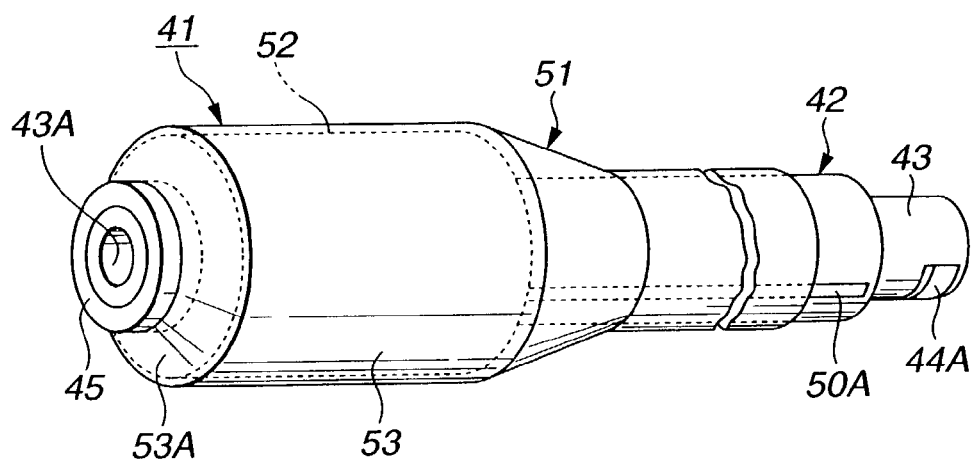

Then, second diffusion layer 53 is formed by plasma spraying of a porous ceramic material on the sintered assembly in a manner similar to the first embodiment to fully cover first diffusion layer 52 and heater covering layer 45, as shown in FIG. 20.

As stated above, the second air/fuel ratio detection sensor is characterized in that solid electrolyte layer 47 has a two-layer structure, inner and outer electrolyte layers 47A, 47B and that a part of outer electrolyte layer 47B is sandwiched between inner and outer electrodes 48, 49 in the radial direction. With this, it is possible to have a wider width for inner and outer electrodes 48, 49 in the axial direction, thereby enlarging the area of these electrodes. Furthermore, it is possible to shorten the distance between these electrodes. This makes it possible to decrease resistance (corresponding to resistance Rp in the above expression (2)) between electrodes 48, 49. Therefore, it is possible to increase the temperature of solid electrolyte layer 47 with a shorter time after engine starts. Furthermore, it is possible to have a longer distance between reference electrode 50 and inner or outer electrode 48 or 49, thereby preventing adverse effect of pump voltage (applied between inner and outer electrodes 48, 49) on reference electrode 50. Still furthermore, it is possible to improve inner and outer electrodes 48, 49 in durability and lifetime, since the above-mentioned chemical reactions of the formulas (1)-(6) proceed at the entire surface of each electrode.

Similar to the first embodiment, it is easily possible to adjust gas diffusion resistance and the like by changing the thickness of second diffusion layer 53. Furthermore, it is also possible to adjust gas diffusion resistance and the like by grinding, for example, end surface 53A (see FIGS. 15 and 20) of second diffusion layer 53 by grinding with diamond.

In the first and second embodiments, core pipes 23, 43 may be formed by extrusion besides injection molding. These core pipes may have a solid structure as opposed to the above-mentioned hollow structure.

The entire contents of basic Japanese Patent Application 2001-282185 (filed Sep. 17, 2001) of the application, of which priority is claimed, are incorporated herein by reference.

What is claimed is:

1. An air/fuel ratio detection apparatus comprising:
a heater portion that has an elongate cylindrical shape and heats by applying electricity to the heater portion from an outside source;
a solid electrolyte layer formed on and surrounding an outer periphery of the heater portion, the solid electrolyte layer being activated by heat from the heater portion to conduct oxygen ions through the solid electrolyte layer;
first and second electrodes that are in contact with an outer periphery of the solid electrolyte layer and are disposed away from each other such that a pumping voltage supplied from an outside source is applied by the first and second electrodes to the solid electrolyte layer, the first and second electrodes being disposed away from each other by a first distance;
a reference electrode for outputting an air/fuel ratio detection signal in relation to one of the first and second electrodes, the reference electrode being formed on the an outer periphery of the solid electrolyte layer and being disposed away from the first and second electrodes; and a diffusion layer made of a porous material, the diffusion layer being formed on and surrounding a periphery of the solid electrolyte layer to cover the first and second electrodes and the reference electrode
wherein the first electrode is disposed closer to the reference electrode than the second electrode,
wherein the first electrode and the reference electrode are disposed away from each other by a second distance that is greater than the first distance, and
wherein the diffusion layer comprises:
a first diffusion layer surrounding the periphery of the solid electrolyte layer, said layer forming a sintered assembly with the heater portion and the solid electrolyte layer; and
a second diffusion layer for adjusting a gas diffusion resistance of each of the first and second electrodes relative to an exhaust gas, the second diffusion layer being formed on periphery of the first diffusion layer and being characterized by the structure of a sprayed material,
wherein the first diffusion layer is made of an aluminum oxide material or an aluminum oxide material comprising zirconia, and
wherein the second diffusion layer is made of an aluminum oxide material comprising magnesium oxide.

2. An air/fuel ratio detection apparatus comprising:
a heater portion that has an elongate cylindrical shape and heats by applying electricity to the heater portion from an outside source;
a solid electrolyte layer formed on and surrounding an outer periphery of the heater portion, the solid electrolyte layer being activated by heat from the heater portion to conduct oxygen ions through the solid electrolyte layer, wherein the solid electrolyte layer comprises an inner layer and an outer layer surrounding a periphery of the inner layer,
first and second electrodes, wherein the first electrode is formed on the outer periphery of the inner layer, and the second electrode is formed on an outer periphery of the outer layer, such that a portion of the outer layer is sandwiched between the first and second electrodes in a radial direction of the solid electrolyte layer, said electrodes being disposed away from each other such that a pumping voltage supplied from an outside source is applied by the first and second electrodes to the solid electrolyte layer, and a reference electrode for outputting an air/fuel ratio detection signal in relation to one of the first and second electrodes, wherein the reference electrode is formed on the outer periphery of the outer layer and is away from the second electrode in an axial direction of the solid electrolyte layer, and a diffusion layer made of a porous material, the diffusion layer being formed on and surrounding a periphery of the solid electrolyte layer to cover the first and second electrodes and the reference electrode.

3. An apparatus according to claim 2, wherein the first and second electrodes are disposed away from each other by a first distance,
wherein the first electrode and the reference electrode are disposed away from each other by a second distance,
wherein the second electrode and the reference electrode are disposed away from each other by a third distance,
wherein each of the second and third distances is greater than the first distance.

4. A method for producing an air/fuel ratio detection apparatus, the method comprising the steps of:
(a) forming a cylindrical heater portion about a cylindrical core pipe and forming a solid electrolyte layer on the heater portion;
(b) forming at least one electrolyte layer on an outer periphery of the cylindrical heater portion and forming first and second electrodes and a reference electrode on an outer periphery of said at least one electrolyte layer such that the first and second electrodes and the reference electrode are in contact with an outer peripheral surface of said at least one solid electrolyte layer;
(c) forming a first diffusion layer on the solid electrolyte layer to cover the first and second electrodes and the reference electrode, thereby making an assembly comprising the heater portion, the solid electrolyte, the first and second electrodes and the reference electrode, and the first diffusion layer;
(d) sintering the assembly into a sintered assembly; and
(e) forming a second diffusion layer on the first diffusion layer of the sintered assembly by a thermal spraying of a ceramic material, the first and second diffusion layers constituting the diffusion layer of the air/fuel ratio detection apparatus.

5. A method according to claim 4, wherein the step (d) is conducted at a temperature of from about 1,3000° C. to about 1,5000° C.

6. A method according to claim 4, wherein, in the step (e), the second diffusion layer is made to have a thickness such that a gas diffusion resistance of each of the first and second electrodes relative to an exhaust gas is adjusted.

7. A method according to claim 4, wherein, in the step (c), a paste of an aluminum oxide comprising zirconia is applied to the solid electrolyte layer to form the first diffusion layer.

8. A method according to claim 4, wherein, in the step (e), an aluminum oxide comprising magnesium oxide is applied to the first diffusion layer to form the second diffusion layer.

9. A method according to claim 4, wherein the method further comprises the steps of:
(f) measuring a characteristic of pumping current between the first and second electrodes of the sintered assembly of the step (d); and
(g) determining thickness of the second diffusion layer to be formed in the step (e), in accordance with the characteristic of the step (f).

10. An air/fuel ratio detection apparatus comprising:
a heater portion that has an elongate cylindrical shape and heats by applying electricity to the heater portion from an outside source;
a solid electrolyte layer formed on and surrounding an outer periphery of the heater portion, the solid electrolyte layer being activated by heat from the heater portion to conduct oxygen ions through the solid electrolyte layer;
first and second electrodes that are in contact with an outer periphery of the solid electrolyte layer and are disposed away from each other such that a pumping voltage supplied from an outside source is applied by the first and second electrodes to the solid electrolyte layer, the first and second electrodes being disposed away from each other by a first distance;
a reference electrode for outputting an air/fuel ratio detection signal in relation to one of the first and second electrodes, the reference electrode being formed on the an outer periphery of the solid electrolyte layer and being disposed away from the first and second electrodes; and a diffusion layer made of a porous material, the diffusion layer being formed on and surrounding a periphery of the solid electrolyte layer to cover the first and second electrodes and the reference electrode
wherein the first electrode is disposed closer to the reference electrode than the second electrode,
wherein the first electrode and the reference electrode are disposed away from each other by a second distance that is greater than the first distance, and
wherein the diffusion layer comprises:
a first diffusion layer surrounding the periphery of the solid electrolyte layer, said layer forming a sintered assembly with the heater portion and the solid electrolyte layer; and
a second diffusion layer for adjusting a gas diffusion resistance of each of the first and second electrodes relative to an exhaust gas, the second diffusion layer being formed on periphery of the first diffusion layer and being characterized by the structure of a sprayed material,
wherein the first diffusion layer has a porosity that is higher than that of the second diffusion layer.

* * * * *